(12) United States Patent
Yang et al.

(10) Patent No.: US 7,769,451 B2
(45) Date of Patent: Aug. 3, 2010

(54) METHOD AND APPARATUS FOR OPTIMIZING CARDIAC RESYNCHRONIZATION THERAPY

(75) Inventors: Zhongping Yang, Woodbury, MN (US); Mark A. Hjelle, White Bear Lake, MN (US); Douglas S. Hine, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 609 days.

(21) Appl. No.: 11/116,547

(22) Filed: Apr. 28, 2005

(65) Prior Publication Data

US 2006/0247692 A1 Nov. 2, 2006

(51) Int. Cl.
 *A61N 1/365* (2006.01)
 *A61B 5/05* (2006.01)
(52) U.S. Cl. .......................... 607/17; 600/345
(58) Field of Classification Search ............... 607/18, 607/22, 23
See application file for complete search history.

(56) References Cited

U.S. PATENT DOCUMENTS

| | | | |
|---|---|---|---|
| 2,214,326 A | 9/1940 | Gregory | |
| 2,305,546 A | 12/1942 | Migrdichian | |
| 5,000,190 A * | 3/1991 | Petre | 600/526 |
| 5,158,078 A | 10/1992 | Bennett et al. | |
| 5,224,475 A | 7/1993 | Berg et al. | |
| 5,226,513 A | 7/1993 | Shibayama | |
| 5,314,448 A | 5/1994 | Kroll et al. | |
| 5,318,593 A | 6/1994 | Duggan | |
| 5,366,485 A | 11/1994 | Kroll et al. | |
| 5,372,607 A * | 12/1994 | Stone et al. | 607/30 |
| 5,564,434 A | 10/1996 | Halperin et al. | |
| 5,634,720 A | 6/1997 | Gallup et al. | |

(Continued)

FOREIGN PATENT DOCUMENTS

WO WO0176469 10/2001

(Continued)

OTHER PUBLICATIONS

Sinha et al., "Usefulness of Brain Natriuretic Peptide Release as a Surrogate Marker of Efficacy of Long-Term Cardiac Resynchronization Therapy in Patients with Heart Failure", Am Journal of Cardiology, Mar. 15, 2003, pp. 755-758, vol. 91.

(Continued)

*Primary Examiner*—Carl H. Layno
*Assistant Examiner*—Jon-Eric C. Morales
(74) *Attorney, Agent, or Firm*—Stephen W. Bauer (57) ABSTRACT

In some embodiments, a method for optimizing cardiac resynchronization therapy (CRT) may include one or more of the following steps: (a) conducting a baseline measurement of a physical parameter of a patient before initiating CRT, (b) performing an implantation process including implanting a pacing device and pacing leads in the patient, the pacing device and pacing leads for providing the CRT, (c) initiating CRT on the patient, (d) measuring the physical parameter of the patient after initiation of the CRT, (e) comparing the measured physical parameter after initiation of the CRT to the baseline measure of the physical parameter to analyze the patient's response to the CRT, (f) adjusting the CRT during the implantation process to try and improve the patient's response to the CRT, and (g) repositioning at least one of the patient leads during the implantation process to try and improve the patient's response to the CRT.

17 Claims, 8 Drawing Sheets

U.S. PATENT DOCUMENTS

| | | |
|---|---|---|
| 5,713,924 A | 2/1998 | Min et al. |
| 5,835,975 A | 11/1998 | Peeters et al. |
| 6,070,101 A | 5/2000 | Struble et al. |
| 6,081,748 A | 6/2000 | Struble et al. |
| 6,122,545 A | 9/2000 | Struble et al. |
| 6,223,082 B1 | 4/2001 | Bakels et al. |
| 6,482,154 B1 | 11/2002 | Haubrich et al. |
| 6,766,189 B2 | 7/2004 | Yu et al. |
| 6,832,113 B2 | 12/2004 | Belalcazar et al. |
| 6,871,088 B2 | 3/2005 | Chinchoy |
| 6,885,889 B2 | 4/2005 | Chinchoy |
| 6,934,586 B2 | 8/2005 | Struble et al. |
| 6,994,676 B2 | 2/2006 | Mulligan et al. |
| 7,027,866 B2 * | 4/2006 | Warkentin .................... 607/23 |
| 7,069,079 B2 | 6/2006 | Struble et al. |
| 7,074,194 B2 * | 7/2006 | Crosby et al. ............... 600/508 |
| 7,092,759 B2 | 8/2006 | Nehls et al. |
| 7,096,064 B2 | 8/2006 | Deno et al. |
| 7,127,290 B2 * | 10/2006 | Girouard et al. .............. 607/17 |
| 7,142,919 B2 | 11/2006 | Hine et al. |
| 7,164,948 B2 | 1/2007 | Struble et al. |
| 7,203,541 B2 | 4/2007 | Sowelam et al. |
| 7,239,915 B2 | 7/2007 | Cohen |
| 7,269,460 B2 | 9/2007 | Chinchoy |
| 2002/0143264 A1 | 10/2002 | Ding et al. |
| 2002/0161307 A1 | 10/2002 | Yu et al. |
| 2003/0055461 A1 * | 3/2003 | Girouard et al. .............. 607/17 |
| 2003/0060851 A1 | 3/2003 | Kramer et al. |
| 2004/0097788 A1 | 5/2004 | Mourlas et al. |
| 2004/0106954 A1 * | 6/2004 | Whitehurst et al. ............ 607/3 |
| 2004/0215252 A1 * | 10/2004 | Verbeek et al. ................ 607/9 |
| 2005/0070768 A1 | 3/2005 | Zhu et al. |
| 2005/0165324 A1 | 7/2005 | Receveur et al. |

FOREIGN PATENT DOCUMENTS

| | | |
|---|---|---|
| WO | WO02083913 | 10/2002 |
| WO | WO2005018737 | 3/2005 |

OTHER PUBLICATIONS

Perego et al., "Simultaneous vs. sequential biventricular pacing in dilated cardiomyopathy: an acute hemodynamic study", European Journal of Heart Failure, 2003, pp. 305-313, 5.

"A Practical Guide to cardiac Pacing", Fifth Edition, Chapter 9, Lippincott, Williams & Wilkins.

* cited by examiner

Blood sampling port

FIG. 7A

Biochemical sensors

FIG. 7B

Mechanical sensors

FIG. 7C

METHOD AND APPARATUS FOR OPTIMIZING CARDIAC RESYNCHRONIZATION THERAPY

FIELD

The present invention relates generally to a method and apparatus for administering therapy for heart failure and, more particularly, to a method and apparatus for predicting optimal cardiac resynchronization therapy (CRT) delivery by determining and analyzing multiple acute responses (e.g., cardiac physiological parameters) at implant.

BACKGROUND

Various medical procedures have been developed to address heart disorders. In particular, CRT can be used to improve the conduction pattern and sequence of the heart. CRT involves the use of an implantable medical device (IMD) that is surgically implanted within the patient's body. Leads from the IMD can be affixed at a desired location within the heart to effectuate synchronous atrial and/or ventricular contractions. Typically, the location of the leads (e.g., therapy site) is selected based upon the anatomy, and disease type, disease severity and/or location of the blockage. Electrical stimulation signals can be delivered to resynchronize the heart, thereby, improving cardiac performance.

Despite these advantages, several shortcomings exist that limit the usefulness of CRT. Hemodynamic response to CRT typically varies from patient to patient, ranging from very positive (e.g., improvement) to substantially negative (e.g., deterioration) based upon the stimulation sites chosen to apply CRT as hemodynamic response can vary based upon the stimulation site used to apply CRT and on the timing of impulses (atrial-ventricular and ventricular-ventricular) not just electrode location. Presently, heart failure patients receiving CRT will have three leads placed in their heart. One lead in their right ventricular chamber, another in their right atrial chamber, and then a third lead that goes in their coronary sinus down one of the cardiac main branches or in a left ventricle epicardial position. However, not all patients have branches in the preferred stimulation sites or "sweet spots". Patients vary a lot in their anatomical size of veins, number of veins, location of veins, and tortuosity of veins. Therefore, getting a lead to the sweet spot can be very challenging. A clinician can spend hours upon hours trying to get it to the right pacing spot. Even with all this work, present studies show only two-thirds of these patients respond to the CRT therapy. This can be due to patients having ischemia of heart tissue which can change the activation sequence in their pacing. Therefore, after implantation one patient may receive a great benefit from the CRT and another having ischemia in a certain area may not receive this benefit.

Presently the existing techniques and/or procedures to determine whether a specific patient will derive an acute hemodynamic benefit from CRT, are unable to determine or validate that a specific stimulation site will produce a positive hemodynamic response from CRT. For example, in order to determine acute hemodynamic benefits from CRT, the patient typically must be screened prior to receiving the therapy and the actual stimulation site used to apply CRT would be validated for each patient. In another method, the day after surgery the clinician will take the patient to an AV optimization setting to look at the timing between the right atrial contraction and the right ventricular contraction. Then the clinician can program the implantable device to obtain the best possible cardiac output or ejection fracture by timing right ventricular contractions and left ventricular contractions making them either simultaneous or sequential delay to improve the cardiac output as much as possible. However, as above, if the patient has ischemia of the heart tissue, the hemodynamics of the heart can only be optimized so much.

SUMMARY

In some embodiments, a method for optimizing CRT may include one or more of the following steps: (a) conducting a baseline measurement of a physical parameter of a patient before initiating CRT, (b) performing an implantation process including implanting a pacing device and pacing leads in the patient, the pacing device and pacing leads for providing the CRT, (c) initiating CRT on the patient, (d) measuring the physical parameter of the patient after initiation of the CRT, (e) comparing the measured physical parameter after initiation of the CRT to the baseline measure of the physical parameter to analyze the patient's response to the CRT, (f) adjusting the CRT during the implantation process to try and improve the patient's response to the CRT, and (g) repositioning at least one of the patient leads during the implantation process to try and improve the patient's response to the CRT.

In some embodiments, a method for optimizing cardiac resynchronization therapy (CRT) may include one or more of the following steps: (a) conducting a baseline measurement of a physical parameter of a patient before initiating CRT, (b) performing an implantation process including implanting a pacing device and pacing leads in the patient, the pacing device and pacing leads for providing the CRT, (c) initiating CRT on the patient, (d) measuring the physical parameter of the patient after initiation of the CRT, (e) repositioning at least one of the patient leads during the implantation process, (f) measuring the physical parameter of the patient after repositioning at least one of the patient leads, and (g) comparing the physical parameter measured after initiation of the CRT and after repositioning at least one of the patient leads to the baseline measurement to determine the preferred location of the last one of the patient leads.

In some embodiments, a lead delivery catheter for implanting patient cardiac leads may include one or more of the following elements: (a) a lead delivery port at a proximal end of the catheter, (b) a lead outlet port at a distal end of the catheter, (c) a means for measuring a B-type Neurouretic Peptide (BNP) concentration level in the patient's blood located proximate the distal end of the catheter, and (d) a means for measuring blood pressure levels in the patient's blood located proximate the distal end of the catheter.

DESCRIPTION OF VARIOUS EMBODIMENTS

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

A system constructed and operated according to embodiments of the invention that may be used to deliver the therapies discussed above may include a signal generator, timing circuit, and/or microprocessor control circuit of the type included in existing pacemaker or ICD systems as is known in the art. Exemplary systems are shown in U.S. Pat. Nos. 5,158,078, 5,318,593, 5,226,513, 5,314,448, 5,366,485, 5,713,924, 5,224,475 and 5,835,975 each of which is incorporated herein by reference, although any other type of pacing and/or ICD system may be used for this purpose. In such systems, EGM sensing is performed by electrodes carried on leads placed within the chambers of the heart, and/or on the housing of the device. Alternatively, subcutaneous and/or external pad or patch electrodes may be used to sense cardiac signals. Physiological sensors may likewise be carried on lead systems according to any of the configurations and/or sensing systems known in the art.

The following introductory material is intended to familiarize the reader with the general nature and some of the features of embodiments of the invention.

All embodiments of the invention share a common need for electrode configurations to deliver electrical stimulation energy where necessary and to time the delivery of this energy to achieve beneficial effects while avoiding unsafe delivery. For each therapy component described below, specific electrode locations and geometries may be preferred. The locations for the electrodes of these teachings for stimulation include: use of large surface area defibrillation coil electrodes in the heart or adjacent to the heart; pacing electrodes at locations including RV apex, outflow tract, atrial locations, HIS bundle site, left side epicardium, pericardium or endocardium; sympathetic nerve regions near the cervical or thoracic spine or nerves or adjacent vessels on or near the heart; transthoracic electrodes including paddles and patches, can electrode, temporary electrodes (e.g., epicardial, transvenous or post-operative electrodes), subcutaneous electrodes and multiple site stimulation.

In accordance with common biomedical engineering practices, stimulation therapy is applied with minimized net charge delivery to reduce corrosion and counteract polarization energy losses. Both energy efficient therapy delivery and electrogram (EGM) sensing benefit from low polarization lead systems. Finally, the electrodes are preferably connected to fast recovery amplifiers that allow EGM sensing soon after therapy delivery.

The most fundamental sensors are those based on electrograms (ECG or EGMs) and reflect cardiac electrical activity. These sensors require electrodes located where they can readily detect depolarization and repolarization signals as well as sense amplifiers for the monitoring of heart rhythm and diagnosis of arrhythmias.

According to one embodiment, blood pressure sensors, accelerometers, flow probes, microphones, or sonometric crystals may be used to measure flow, force, velocity, movement of the walls of the heart, and/or to estimate the volume of the cardiac chambers. Parameters derived from these sensors can also be used to detect the onset and severity of cardiac hemodynamic dysfunction. For example, HF decompensation may be indicated when a change in long-term diastolic cardiac pressure has increased while contractility of the heart derived from dP/dt rate of rise of ventricular pressure has diminished. Another embodiment of the invention may utilize changes in transthoracic or intracardiac impedance signals to sense cardiac motion and respiratory movement. Metabolic or chemical sensors such as expired $CO_2$ and blood oxygen saturation, pH, $pO_2$, and/or lactate may be employed to reflect cardiac dysfunction.

Other signals such as surface electrocardiogram (ECG) or electrogram (EGM) signals from electrodes within the patient's body may be used to detect dysfunction and heart failure (HF). For example, the ST segment level of a cardiac cycle (PQRST) detected by an ECG may be monitored. An elevated or depressed ST segment level has been found to be reliable indicator of ischemia, a condition known to be associated with dysfunction and HF. Alternatively, the duration of the Q-T interval may also be used to detect hemodynamic dysfunction. For example, a shortened Q-T interval may indicate myocardial dysfunction. A template-matching algorithm such as a wavelet classification algorithm may be used to identify electrogram signals that are associated with hemodynamic dysfunction.

Chemical sensors may be used to initiate therapy, including sensors that analyze the blood to detect changes in B-type Neurouretic Peptide (BNP), lactate, $O_2$ saturation, $PO_2$, $PCO_2$, neurohormones, and pH. Expired gas may be analyzed for $PCO_2$ as an indicator of cardiac output during resuscitation procedures. Pulse oximetry may provide noninvasive assessments of oxygen saturation and pulse plethysmogram signals.

Although pressure sensors figure prominently in the examples above a number of other sensors could reflect mechanical function. Intracardiac or transthoracic impedance changes reflect mechanical function, stroke volume, and cardiac output. Accelerometers or microphones within the body or applied externally sense serious cardiac dysfunction and monitor the response to therapy. Heart volume, dimension changes, and velocities may be measured by implanted or external applications of ultrasound.

Physiologic signals may continue to be sensed to determine if a therapy termination condition is met so that therapy may be terminated. An additional aspect of embodiments of the invention is to include not only a mechanical sensor in or on the heart to detect cardiac function, but a second sensor or a multitude of sensors away from the heart, such as inside the implantable device housing or can (acting as an indifferent electrode). From this second sensor, CPR artifact (due to chest compressions and the like) could be identified and subtracted to reveal a more accurate assessment of true cardiac function.

Figure 1:
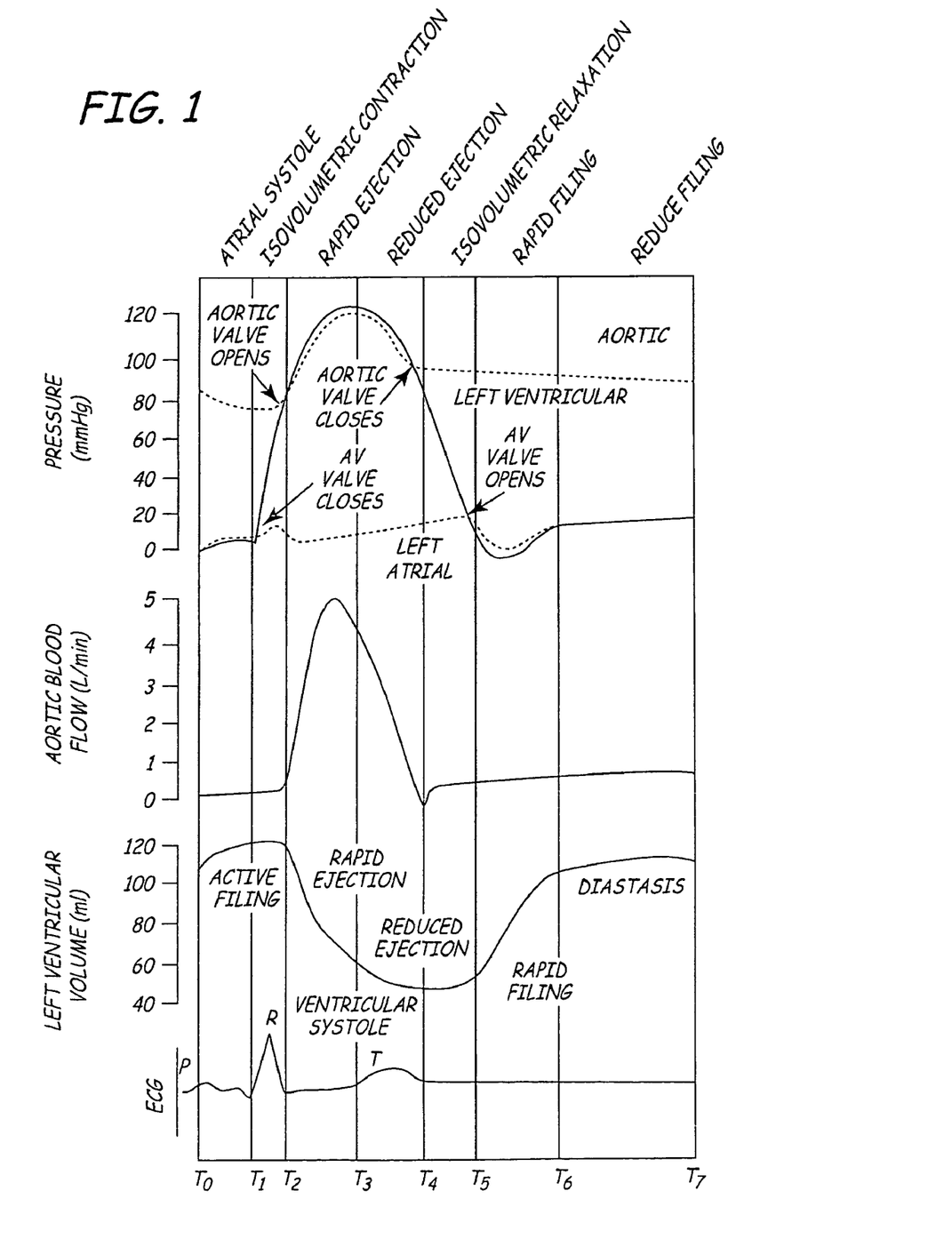
FIG. 1 depicts the relationship of heart chamber EGM, pressure, flow, and volume during a cardiac cycle.

Before describing embodiments of the invention, reference is made to FIG. 1 which depicts the electrical depolarization waves attendant a normal sinus rhythm cardiac cycle in relation to the fluctuations in absolute blood pressure, aortic blood flow and ventricular volume in the left heart. The right atria and ventricles exhibit roughly similar pressure, flow, and volume fluctuations, in relation to the PQRST complex, as the left atria and ventricles. It is understood that the monitoring and stimulation therapy aspects of these teachings may reside and act on either or both sides of the heart. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$-$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony. In FIG. 1 for example, atrial and/or ventricular pacing pulses would precede the P-wave and the deflection of the QRS complex commonly referred to as the R-wave. Cardiac output may be reduced by the inability of the atrial or ventricular myocardial cells to relax following atrial ($T_0$-$T_1$) and ventricular ($T_1$-$T_2$) systolic periods. Prolonged systolic time periods reduce passive filling time $T_4$-$T_7$ as shown in FIG. 1. Thus, the amount of blood expelled from the atria and/or ventricles in the next cardiac cycle may be less than optimum. This is particularly the case with HF patients or other patients in whom the stiffness of the heart is increased, cardiac filling during the passive filling phase (T4-$T_7$) and during atrial systole (T0-$T_1$) is significantly limited.

It will be appreciated from the following description that the monitor/therapy delivery IMD of embodiments of the invention may be utilized to obtain the aforementioned parameters as stored patient data over a period of time and to deliver therapies for treating the heart failure. The physician is able to initiate uplink telemetry of the patient data in order to review it to make an assessment of the heart failure state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including PESP and/or NES stimulation, and pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and the therapies that are delivered.

Accordingly, an embodiment of the invention is disclosed in detail in the context of a multi-chamber pacing system that is modified to derive the aforementioned parameters indicative of cardiac mechanical dysfunction from sensors, sense electrodes and electrical stimulation electrodes located in operative relation to one or more heart chamber. This embodiment of the invention may be programmed to operate as an AV sequential, bi-atrial and bi-ventricular, pacing system operating in demand, atrial tracking, and triggered pacing for restoring synchrony in depolarizations and contraction of left and right ventricles in synchronization with atrial sensed and paced events for treating HF and/or bradycardia. This embodiment of the invention is therefore programmable to operate as a two, three or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described below can be selectively programmed to function or physically only incorporated into a simpler, single chamber, monitoring/stimulation system for deriving the parameters indicative of heart failure state.

Figure 2:
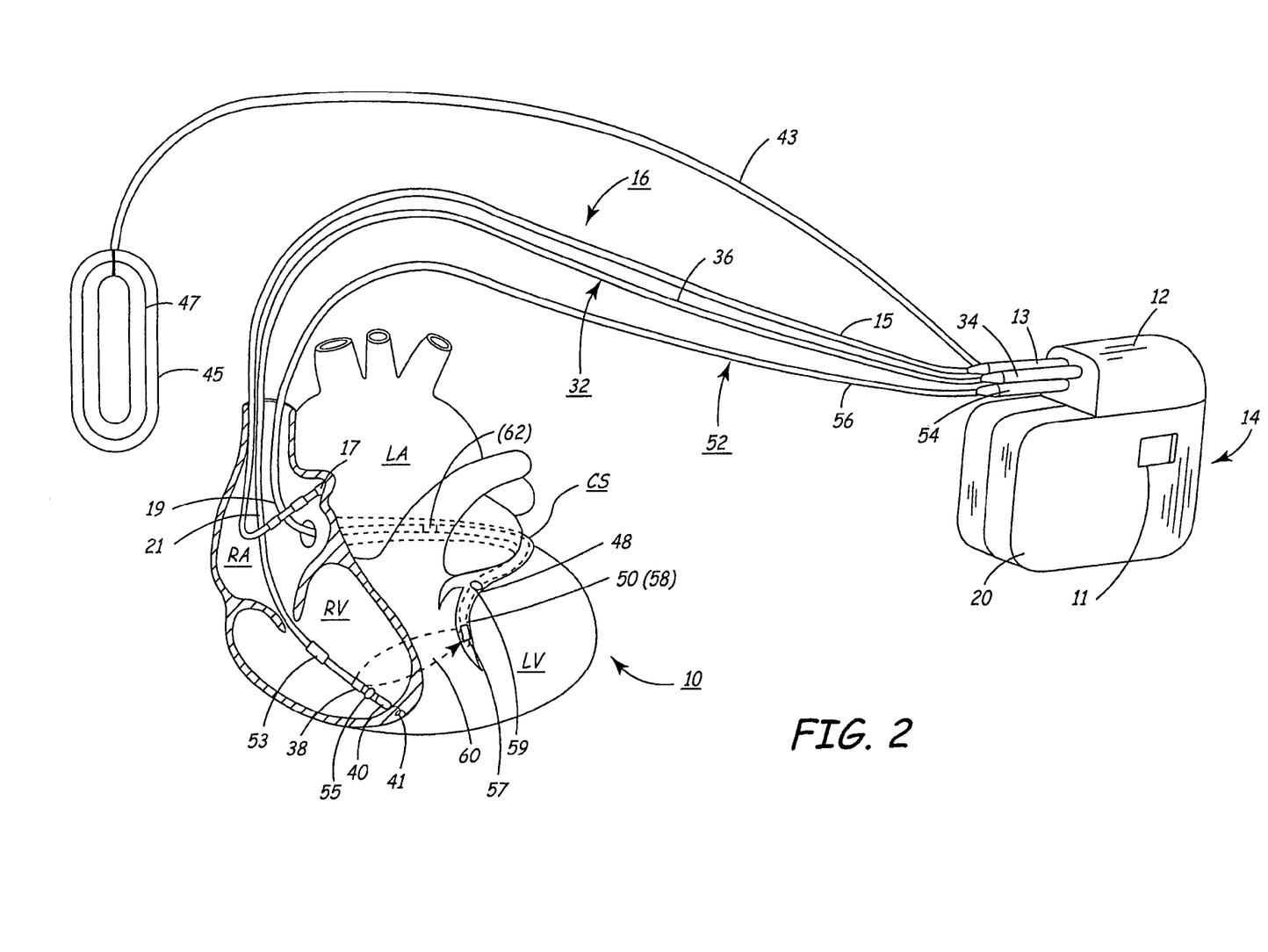
FIG. 2 is a schematic diagram depicting a multi-channel, atrial and bi-ventricular, monitoring/pacing IMD in which embodiments of the invention is preferably implemented.

In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiority into branches of the great vein. The cardiac cycle commences normally with the generation of the depolarization impulse at the SA Node in the right atrial wall. The impulse then conducts through the right atrium by way of Internodal Tracts, and conducts to the left atrial septum by way of Bachmann's Bundle. The RA depolarization wave reaches the Atrio-ventricular (AV) node and the atrial septum within about 40 msec and reaches the furthest walls of the RA and LA within about 70 msec. Approximately 100 ms following electrical activation, the atria contract. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence becomes highly disrupted in patients suffering from advanced HF and exhibiting Intra-atrial conduction delay (IACD), Left Bundle Branch Block (LBBB), Right Bundle Branch Block (RBBB), and/or Intraventricular Conduction Delay (IVCD). These conduction defects give rise to great asynchrony between RV activation and LV activation. Inter-ventricular asynchrony can range from 80 to 200 msec or longer. In RBBB and LBBB patients, the QRS complex is widened far beyond the normal range to between 120 msec and 250 msec as measured on surface ECG. This increased width demonstrates the lack of synchrony of the right and left ventricular depolarizations and contractions.

FIG. 2 also depicts an implanted, multi-channel cardiac pacemaker, ICD, IPG or other IMD of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32, and 52 connect the IPG 14 with the RA, the RV, and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. For example, bipolar left ventricle (LV) leads and LV leads with dual stimulation electrodes (changing from one cathode to a second cathode without "repositioning") are now available. Also LV leads with fixation are contemplated to reduce dislodgment or migration of the LV electrode. Also, LV leads do not necessarily need to be placed "deep" in the vein branch.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

Moreover, in a four-chamber embodiment, LV CS lead 52 could bear a proximal LA CS pace/sense electrode positioned along the lead body to lay in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Typically, in pacing/defibrillation systems of the type illustrated in FIG. 2, the electrodes designated above as "pace/sense" electrodes are used for both pacing and sensing functions. In accordance with one aspect of embodiments of the invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate. With respect to embodiments of the invention, a subcutaneous electrode 45 coupled to medical electrical lead 43 may be added to or substituted for one or more of the leads or electrodes depicted in FIG. 2. If a subcutaneous electrode 45 is utilized, a suitable defibrillation coil 47 may be coupled to appropriate high voltage circuitry to deliver a timed defibrillation pulse. While coil electrode 53 is depicted coupled to a portion of RV lead 32, such an electrode may be coupled to other portions of any of the leads depicted in FIG. 2, such as LV electrode 57. The coil electrode 53, subcutaneous electrode 45 or other types of suitable electrode configurations may be electrically coupled to low voltage pacing/sensing circuitry in addition to high voltage circuitry. As is known, such electrodes may be disposed in a variety of locations in, around, and on the heart.

Also depicted in FIG. 2 is an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 may comprise an accelerometer, an impedance electrode, a saturated oxygen sensor, a pH sensor, and the like. In addition, each of the leads could carry a mechanical sensor for developing systolic and diastolic pressures and a series of spaced apart impedance sensing leads for developing volumetric measurements of the expansion and contraction of the RA, LA, RV and LV.

Of course, such sensors must be rendered biocompatible and reliable for long-term use. In addition, one or more sensors may be disposed in or on the housing 20 of IMD 14 such as sensor 11 depicted in FIG. 2.

Figure 3A:
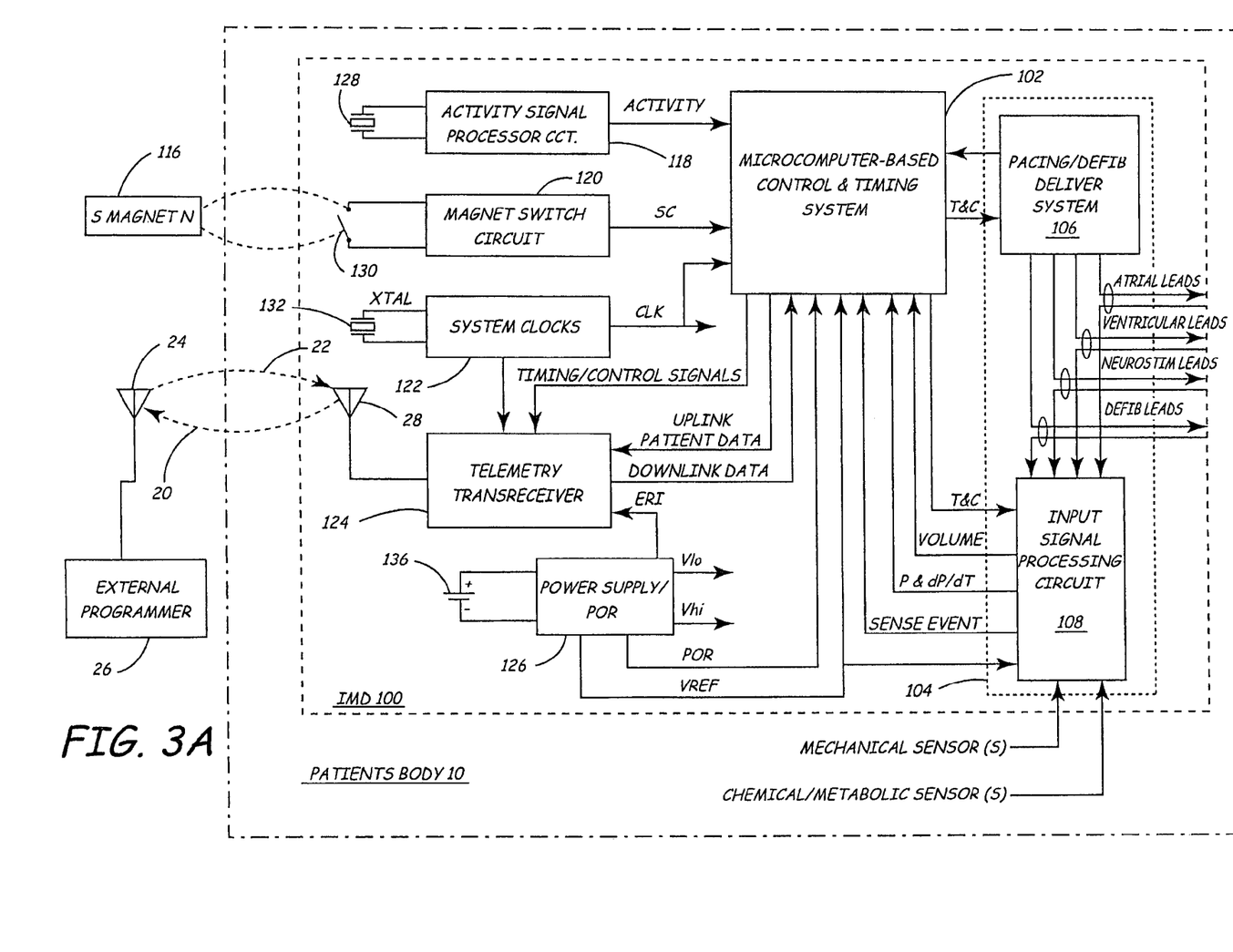
FIG. 3A is a simplified block diagram of one embodiment of IPG circuitry and associated leads employed in the system of FIG. 1 enabling selective therapy delivery and heart failure state monitoring in one or more heart chamber.

FIG. 3A depicts a system architecture of an exemplary multi-chamber monitor/sensor 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters, which will cause a change in the detection or response of such algorithms. Oftentimes, discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed microcomputer.

The multi-chamber monitor/sensor 100 also typically includes patient interface circuitry 104 for receiving signals from sensors and pace/sense electrodes located at specific sites of the patient's heart chambers and/or delivering stimulation to derive heart failure parameters or a pacing therapy to the heart chambers. The patient interface circuitry 104 therefore comprises a stimulation delivery system 106 optionally including pacing and other stimulation therapies and a physiologic input signal processing circuit 108 for processing the blood pressure and volumetric signals output by sensors. For purposes of illustration of the possible uses of embodiments of the invention, a set of lead connections are depicted for making electrical connections between the therapy delivery system 106 and the input signal processing circuit 108 and sets of pace/sense electrodes located in operative relation to the RA, LA, RV and LV.

As depicted in FIG. 3A, chemical/metabolic sensor input and/or mechanical sensor inputs are provided to the input signal processing circuit 108. As described with respect to FIG. 2, a wide variety of such sensors may be utilized when practicing embodiments of the invention.

A battery provides a source of electrical energy to power the multi-chamber monitor/sensor operating system including the circuitry of multi-chamber monitor/sensor 100 and to power any electromechanical devices, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3A, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber monitor/sensor 100, uplink and downlink telemetry capabilities are provided to enable communication with either a remotely located external medical device or a more proximal medical device on the patient's body or another multi-chamber monitor/sensor in the patient's body as described above with respect to FIG. 2 and FIG. 3A (and FIG. 3B described below). The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes real time sampled signal levels, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ids, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data".

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal-processing channel for sensing and processing a sensor derived signal from a physiologic sensor located in relation to a heart chamber or elsewhere in the body.

Figure 3B:
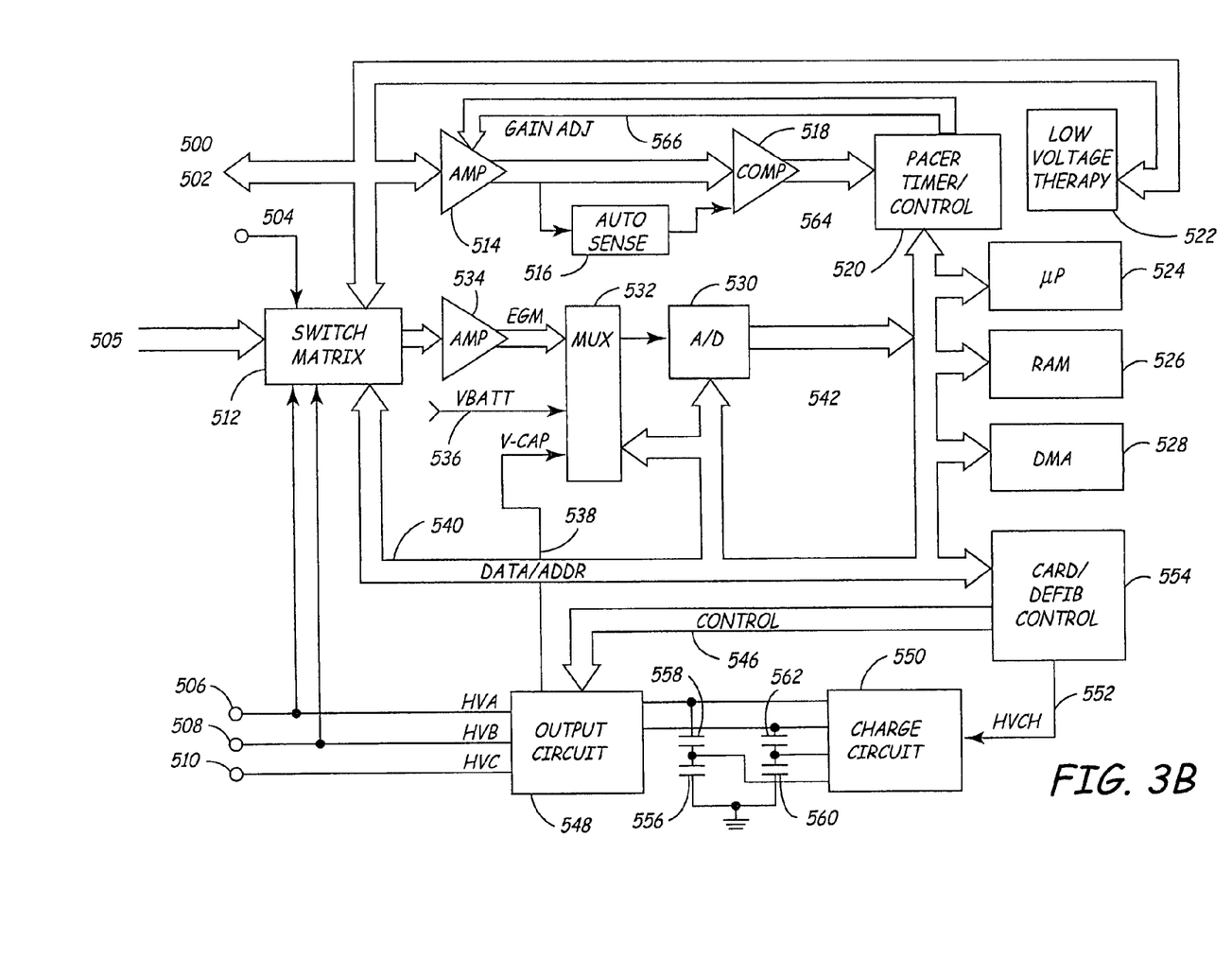
FIG. 3B is a simplified block diagram of another embodiment of IPG circuitry and associated leads employed in the system of FIG. 1 enabling selective therapy delivery and heart failure state monitoring in one or more heart chamber.

Now turning to FIG. 3B, another system architecture for use in conjunction with embodiments of the invention is depicted. FIG. 3B is an exemplary system that may be utilized to deliver therapy by incorporating the system and method described above. Notably, the depicted system includes a sense amplifier 534 to sense electrical signals such as EGM signals using one or more leads placed within a respective chamber of the heart. These signals are used to determine atrial and ventricular depolarizations and Q-T length so that therapy delivery is provided in a safe manner. One or more physiological or hemodynamic signals may be sensed using sensors such as those discussed above. These additional signals, which are shown collectively provided on line 505, may be used to determine cardiac output so that therapy may be initiated, terminated, and/or optimized.

The system of FIG. 3B further includes a timer/controller to control the delivery of pacing pulses on output lines 500 and 502. This circuit, alone or in conjunction with microprocessor 524, controls interval lengths, pulse amplitudes, pulse lengths, and other waveform attributes associated with the pacing pulses. Output circuit 548 delivers high-voltage stimulation such as defibrillation shocks under the control of defibrillation control circuit 554.

Not all of the conventional interconnections of these voltages and signals are shown in either FIG. 3A or FIG. 3B and many other variations on the illustrated electronic circuitry are possible, as is known to those of skill in the art.

Figure 4:
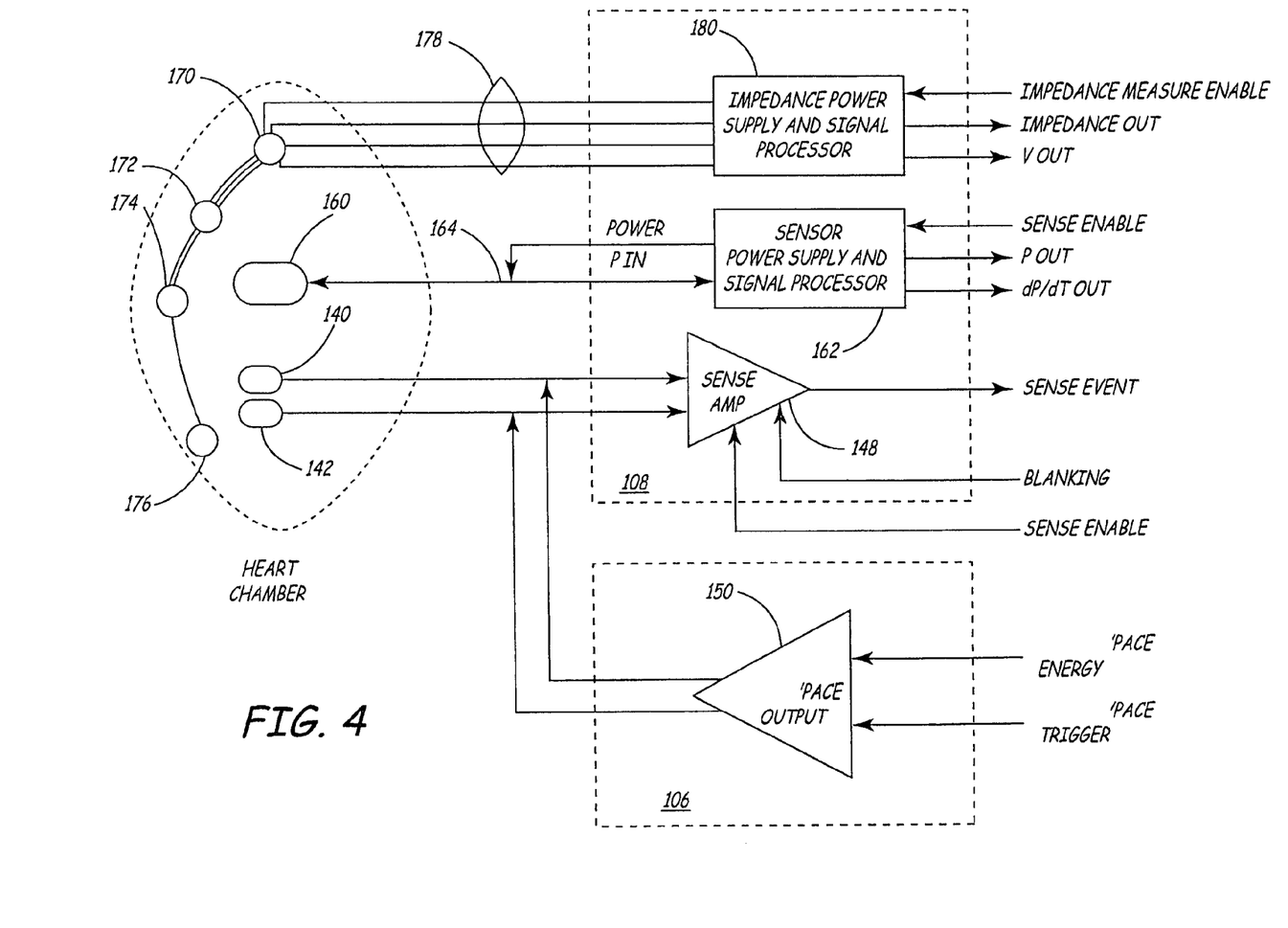
FIG. 4 is a simplified block diagram of a single monitoring and pacing channel for deriving pressure, impedance, and cardiac EGM signals employed in monitoring and optionally pacing the heart in accordance with embodiments of the invention.

FIG. 4 schematically illustrates one pacing, sensing, and parameter measuring channel in relation to one heart chamber. A pair of pace/sense electrodes 140,142, a sensor 160 (e.g., a pressure, saturated oxygen, flow, pH or the like), and a plurality, e.g., four, impedance-measuring electrodes 170, 172,174,176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled. The blanking signal is provided by control and timing system 102 upon delivery of a pacing pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art.

The pair of pace/sense electrodes 140,142 are also coupled through lead conductors 144 and 146, respectively, to the output of a pulse generator 150. The pulse generator 150, within pacing delivery system 106, selectively provides a pacing pulse to electrodes 140,142 in response to a PACE trigger signal generated at the time-out of the EI timer within control and timing system 102 in a manner well known in the pacing art. Or, the pulse generator 150 selectively provides a pulse or pulse train to electrodes 140, 142 in response to a PACE trigger, signal generated at the time-out of an timer within control and timing system 102.

The sensor 160 and/or other physiologic sensor is coupled to a sensor power supply and signal processor 162 within the input signal processing circuit 108 through a set of lead conductors 164 that convey power to the sensor 160 and sampled blood pressure P signals from the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564,434.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art such as having an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

A measure of heart chamber volume V is provided by the set of impedance electrodes 170, 172, 174 and 176 when the impedance power supply and signal processor 180 is enabled by an impedance measure enable signal provided by control and timing system 102. A fixed current carrier signal is applied between the pairs of impedance electrodes and the voltage of the signal is modulated by the impedance through the blood and heart muscle which varies as distance between the impedance electrodes varies. Thus, the calculation of the heart chamber volume V signals from impedance measurements between selected pairs of impedance electrodes 170, 172, 174 and 176 occurs during the contraction and relaxation of the heart chamber that moves the spaced apart electrode pairs closer together and farther apart, respectively, due to the heart wall movement or the tidal flow of blood out of and then into the heart chamber. Raw signals are demodulated, digitized, and processed to obtain an extrapolated impedance value. When this value is divided into the product of blood resistivity times the square of the distance between the pairs of spaced electrodes, the result is a measure of instantaneous heart chamber volume V within the heart chamber.

This invention relates to a method and apparatus optimizing CRT based upon measured acute responses of blood chemicals, hemodynamics, echocardiography and electrocardiography to CRT. The method comprises testing of electrophysiology, hemodynamics and blood biochemicals, such as ECG, echocardiogram and neurohormones, oxygen, metal ions, lactate especially BNP before and after delivering the CRT. The optimized CRT can then be determined by comparing the changes in the ECG, hemodynamics, blood biochemical's concentration in the heart before and after delivery of CRT while implanting CRT devices.

With reference to FIG. 2 once again, a first endocardial RA lead 16 is passed through a vein into the RA chamber of the heart 10, and the distal end of the RA lead 16 is attached to the RA wall by an attachment mechanism 17. A second endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. A third endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. A third lead could also be placed in a LV epicardial position without departing from the spirit of the invention.

The distal end of such LV CS leads is advanced through the superior vena cava, the right atrium, the ostium of the coronary sinus, the coronary sinus, and into a coronary vein descending from the coronary sinus, such as the great vein. Third lead 52 can be the most helpful lead for heart failure patients as this lead will provide the pacing pulse for the LV helping provide synchronous atrial and/or ventricular contractions and thus helping the heart beat more naturally generating greater hemodynamics. However, as stated above, not all patients have branches in the preferred stimulation sites or "sweet spots". In fact, all patients have varying physiology and the sweet spot may be located between veins branching off of the coronary sinus. Patients vary a lot in their anatomical size of veins, number of veins, location of veins, and tortuosity of veins. Therefore, getting a lead to the sweet spot can be very challenging. A clinician can spend hours upon hours trying to get it to the right pacing spot. And, even with all this work, present studies show only two-thirds of these patients are responding to the CRT therapy. This can be due to the clinician simply not locating the sweet spot or patients having ischemia of heart tissue, which can change the activation sequence in the pacing. Therefore, after implantation one patient may receive a great benefit from the CRT and another having ischemia in a certain area may not receive this benefit. While the description is limited to a discussion of proper placement of third lead 52, it is fully contemplated this discussion could be extended to first lead 16 and/or second lead 32 without departing from the spirit of the invention.

Figure 5:
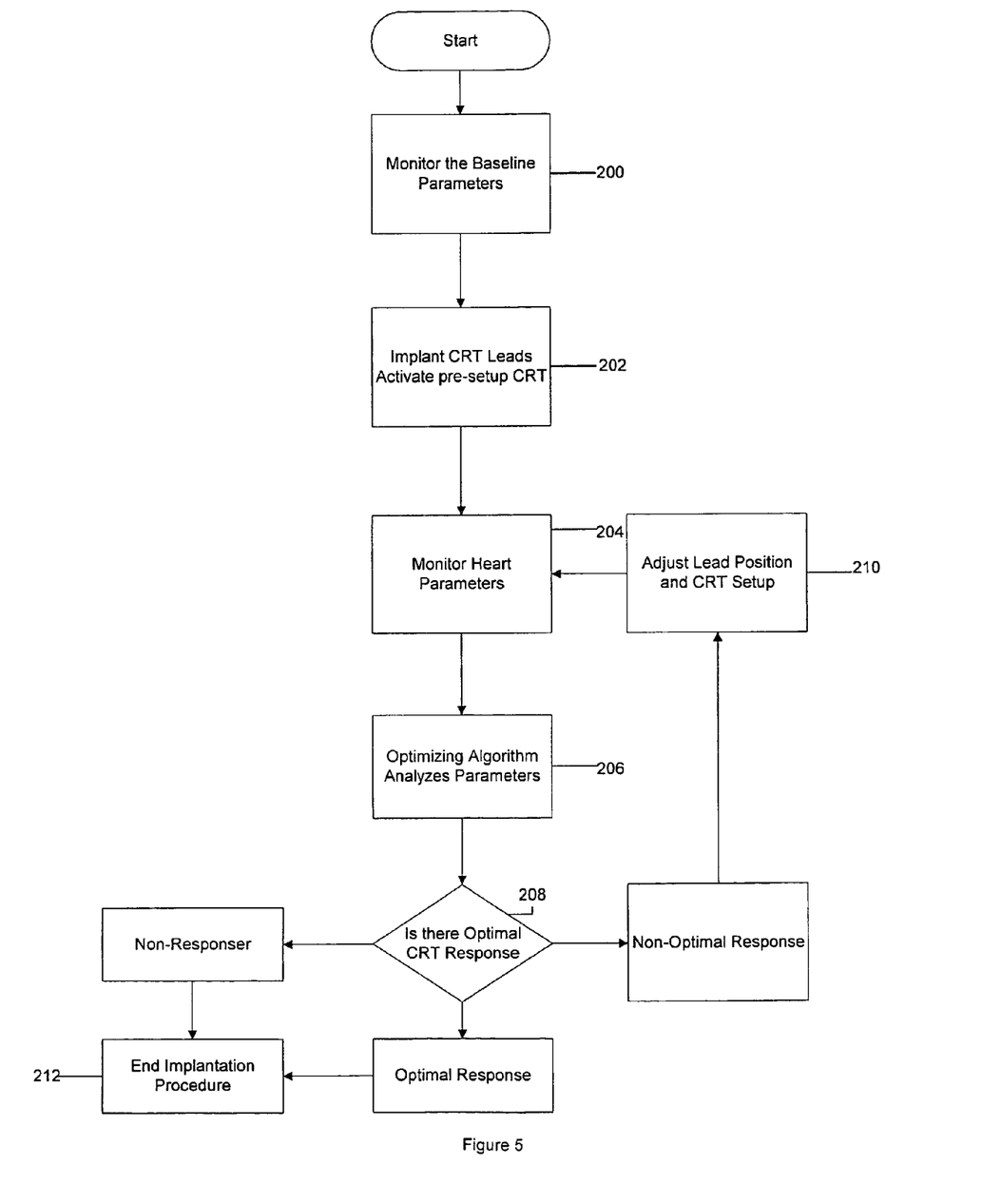
FIG. 5 is a flow diagram of a method for optimizing cardiac resynchronization therapy based upon measured acute responses in an embodiment of the present invention.

With reference to FIG. 5, a flow diagram of a method for optimizing cardiac resynchronization therapy based upon monitored acute responses in an embodiment of the present invention is shown. At state 200 initial baseline parameters are monitored such as ECG, LV & RV pressure, and blood biochemicals before the implantation of leads 16, 32, and 52 and/or before initiation of CRT. These baseline parameters will give an indication of the status of the patient's heart before the implantation of implantable device 14. Implantable device 14 is then implanted and leads 16, 32, and 52 are initially placed in their respective positions as discussed above at state 202. Further, implantable device 14 is initially set up to deliver CRT. During CRT the parameters discussed above are continuously monitored at state 204. The current measured parameters are then compared against the baseline parameters utilizing an algorithm within implantable device 14 at state 206. The algorithm then makes a determination of whether there is an acute response to the CRT at state 208. This algorithm can be analogous to feedbcak loop controller algorithms. The comparison would be based upon whether the parameters showed improved heart performance and hemodynamics. For example, BNP concentrations have been shown to be elevated in patients with symptomatic left ventricular dysfunction correlating to left ventricular filling pressure. Therefore, if the baseline BNP measurement changed, either up or down, after initial CRT, then the algorithm would indicate that the heart's hemodynamics have changed. BNP will typically go up in acute response to good CRT therapy placed at the sweet spot. BNP is created as the result of stress. The heart is working poorly, then CRT is applied correctly to the sweet spot and the heart is now stressed in a new way. Thus, BNP will go up but then settle down if the lead is indeed in the sweet spot. Another example would be the oxygen level. If the baseline oxygen level was low and the initial CRT oxygen level had increased then the algorithm would indicate that the CRT therapy is affecting the heart hemodynamics.

The algorithm then makes a determination on whether the CRT was optimal for the patient. This determination could be based upon physician-inputted parameters. If the algorithm determines that the CRT was non-optimal, the physician is informed of this via an external implantable device programmer. The physician can then suspend CRT, adjust lead 52 moving it to another position or adjust AV timing and VV timing, and reinitiate CRT at state 210. The monitoring and optimizing process is then repeated. If the algorithm determines that the CRT response is optimal, then the physician is notified. The physician can then be confident he has found the optimum location for lead 52 and that implantable device 14 will provide effective CRT for the patient. The physician can then end the implantation procedure at state 212. This optimization procedure insures that the patient receives an implantable device that will work properly without the risk of the implantable device being fully implanted and then not working properly due to some ischemia of the heart or that electrode 50 is simply not in a location which provides for optimum contractility. Additionally, if the optimization process is repeated and a proper placement for lead 52 is never found, then the physician can make the determination that the patient is a non-responder to CRT and end the implantation procedure at step 212.

Figure 6:
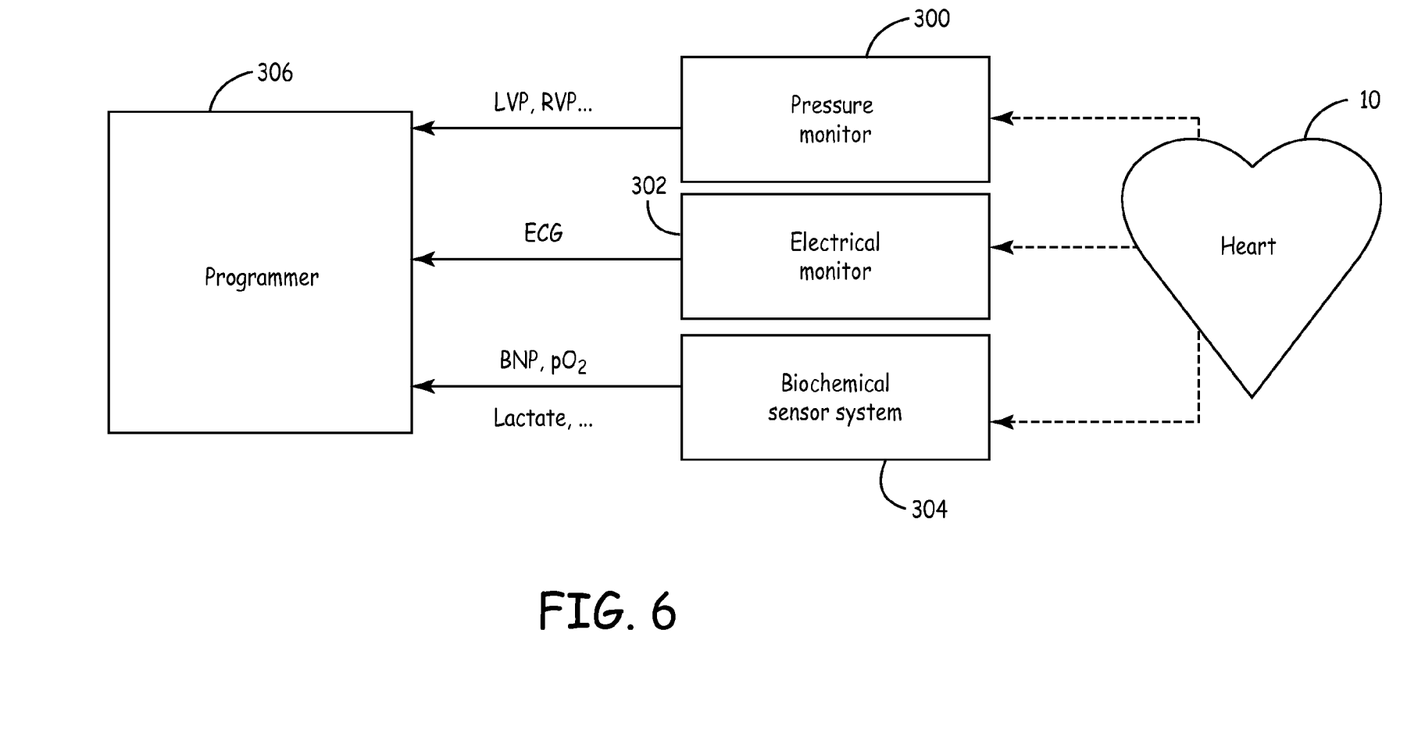
FIG. 6 is a box diagram schematic of a pacing optimization circuit in an embodiment of the present invention.

With reference to FIG. 6, a box diagram schematic of a pacing optimization circuit in an embodiment of the present invention is shown. As shown, heart 10 can be monitored in a plurality of ways to determine how well the heart is working. A pressure sensor 300, such as those discussed above can monitor the right and left ventricular pressure. Electrical sensors 302, such as those discussed above, can monitor the electrical activity of the heart. Biochemical sensors 304 can be used to monitor chemicals, such as BNP, $PO_2$, and lactate within the blood stream. All or some of these heart parameters can then be sent to processor 306, which can be processors 102 or 524 located on board implantable device 14 or can be a processor located on an external programmer such as is discussed in U.S. Pat. No. 6,482,154 titled Long Range Implantable Medical Device Telemetry System with Positive Patient Identification herein incorporated by reference in its entirety. The optimization algorithm discussed can then process the incoming parameters and attempt to optimize the CRT. The algorithm can operate with all, some, or one of the measured heart parameters in the optimization process. However, the more parameters measured and utilized the better. Thus, if the algorithm determines that not just one, but several measured parameters are indicating the heart's hemodynamics has changed the algorithm will indicate this change and begin the optimization process. Likewise, if a majority of the measure parameters are indicating little to no change in the heart's hemodynamics has occurred, then the algorithm will indicate the lead is in a bad position and electrode 50 can be moved to try and obtain an acute response.

Figure 7A:
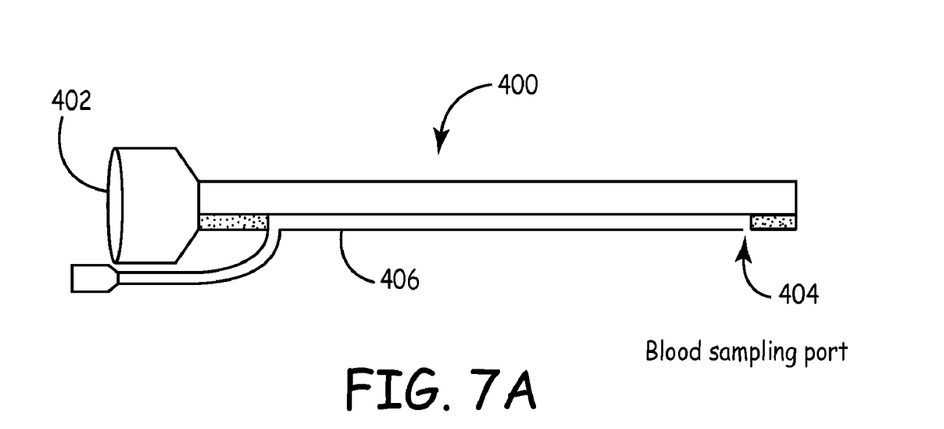
FIG. 7A is a diagram of lead delivery catheter blood sampling device in an embodiment of the present invention.
Figure 7B:
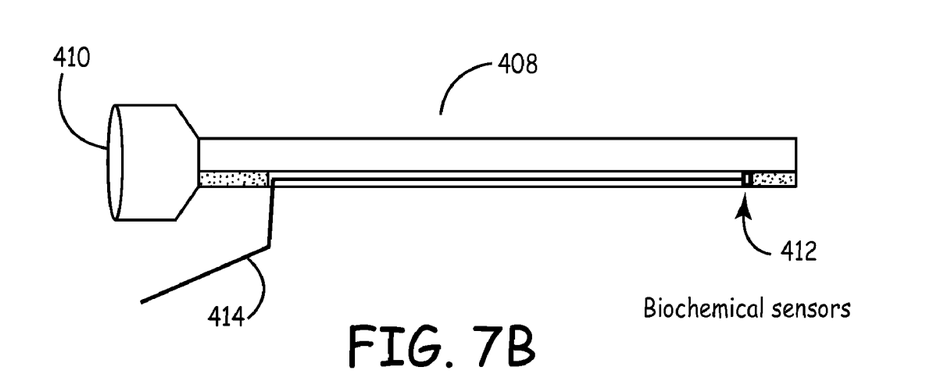
FIG. 7B is a diagram of lead delivery catheter having a biochemical sensor in an embodiment of the present invention.
Figure 7C:
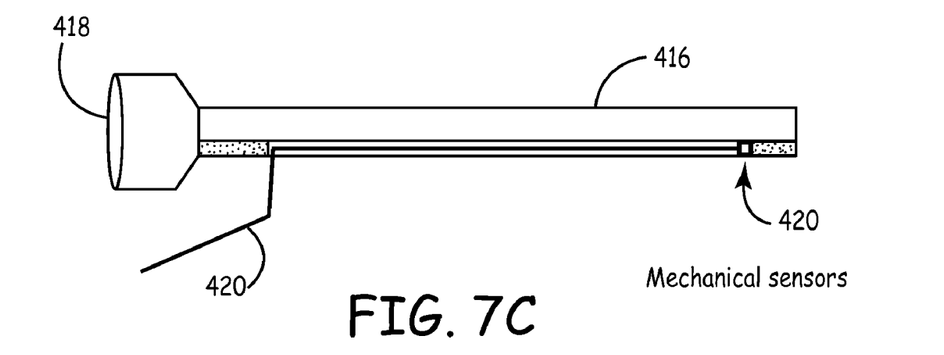
FIG. 7C is a diagram of lead delivery catheter having a pressure sensor in an embodiment of the present invention.

With reference to FIGS. 7A-C, a diagram of lead delivery catheter in an embodiment of the present invention is shown. In FIG. 7A, catheter 400 has a lead delivery port 402 where leads 16, 32, and 52 can be routed through to be implanted within the heart. Additionally catheter 400 can have a blood sampling port 404. When desired, such as obtaining the baseline measurements and after CRT measurements, the physician can sample blood through blood port 404 and tube 406. The physician can then test the blood for various quantities, such as oxygen and metal ions using methods known in the art. Based upon these values the physician can make a determination on whether an acute response has occurred and eliminate the need to use the algorithm. However, the physician can also input the blood values into the programmer for the algorithm to use in accessing whether an acute response has occurred.

In FIG. 7B, catheter 408 has a lead delivery port 410 where leads 16, 32, and 52 can be routed through to be implanted within the heart. Catheter 408 can also have biochemical sensors 412 for detecting BNP and/or lactate using methods known in the art. The biochemical values are then sent up line 414 to an external programmer containing the algorithm discussed above which will begin the optimization process. It's of note that the sensors discussed in this description can be external or internal (meaning part of the implantable device or simply left within the patient) without departing from the spirit of the invention. In addition, the location of the blood monitoring port or sensors (biochemical, pressure, bnp, lactate) can be located anywhere on the catheter 408. Hence measurement of the bio-parameters can occur in the RA or CS. Further, the algorithm can be within implantable device 14 or located on an external programmer.

In FIG. 7C, catheter 416 has a lead delivery port 418 where leads 16, 32, and 52 can be routed through to be implanted within the heart. Catheter 416 can also have pressure sensors 420 for detecting left and/or right ventricular pressure using methods known in the art. The pressure readings are sent up line 422 to an external programmer containing the algorithm discussed above which runs the optimization process. It is of note, that none of the sensors discussed in FIGS. 7A-C need to be located at the distal end of the catheter and can be located anywhere on the catheter without departing from the spirit of the invention.

Thus, embodiments of the METHOD AND APPARATUS FOR OPTIMIZING CARDIAC RESYNCHRONIZATION THERAPY are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for optimizing cardiac resynchronization therapy (CRT), the method comprising:
    conducting a baseline measurement of a physical parameter of a patient before initiating CRT;
    performing an implantation process including implanting a pacing device and pacing leads in the patient, the pacing device and pacing leads for providing the CRT;
    initiating CRT on the patient;
    measuring the physical parameter of the patient after initiation of the CRT;
    comparing the measured physical parameter after initiation of the CRT to the baseline measure of the physical parameter to analyze the patient's response to the CRT; and
    based upon the comparison of the measured physical parameter to the baseline measure of the physical parameter, adjusting the CRT during the implantation process to improve the patient's analyzed response to the CRT, and
    wherein the physical parameter comprises the concentration of a blood biochemical; and wherein the blood biochemical is B-type Neurouretic Peptide (BNP).

2. The method of claim 1, wherein the BNP concentration level is measured from blood taken directly from the patient's heart.

3. The method of claim 1, further including repositioning at least one of the patient leads during the implantation process to try and improve the patient's response to the CRT.

4. The method of claim 3, wherein the at least one of the patient leads is a lead that stimulates a left ventricle of the patient's heart.

5. The method of claim 1, wherein the adjusting the CRT during the implantation process includes adjusting at least one of an AV time interval and a VV time interval.

6. A method for optimizing cardiac resynchronization therapy (CRT), the method comprising:
conducting a baseline measurement of a physical parameter of a patient before initiating CRT;
performing an implantation process including implanting a pacing device and pacing leads in the patient, the pacing device and pacing leads for providing the CRT;
initiating CRT on the patient;
measuring the physical parameter of the patient after initiation of the CRT;
comparing the measured physical parameter after initiation of the CRT to the baseline measure of the physical parameter to analyze the patient's response to the CRT; and
based upon the comparison of the measured physical parameter to the baseline measure of the physical parameter, adjusting the CRT during the implantation process to improve the patient's analyzed response to the CRT,
wherein the physical parameter comprises the concentration of B-type Neurouretic Peptide (BNP),
wherein the BNP concentration level is measured from blood taken directly from the patient's heart, and
wherein measuring the physical parameter of the patient is performed with an elongated lead delivery catheter and said elongated lead delivery catheter includes a means for measuring the patient's BNP concentration level coupled to a portion of said elongated lead delivery catheter.

7. The method of claim 6 wherein adjusting the CRT comprises repositioning a said pacing lead.

8. The method of claim 6, wherein the at least one of the pacing leads is located to stimulate the patient's left ventricle.

9. The method of claim 6, wherein adjusting the CRT comprises adjusting at least one of an AV time interval and a VV time interval.

10. A method for optimizing cardiac resynchronization therapy (CRT), the method comprising:
conducting a baseline measurement of a physical parameter of a patient before initiating CRT;
performing an implantation process including implanting a pacing device and pacing leads in the patient, the pacing device and pacing leads for providing the CRT;
initiating CRT on the patient;
measuring the physical parameter of the patient after initiation of the CRT;
repositioning at least one of the patient leads during the implantation process;
measuring the physical parameter of the patient after repositioning at least one of the patient leads;
comparing the physical parameter measured after initiation of the CRT and after repositioning at least one of the patient leads to the baseline measurement to determine the preferred location of the last one of the patient leads based upon the comparison of the measured physical parameter to the baseline measure of the physical parameter,
wherein the physical parameter comprises the concentration of a blood biochemical.

11. The method of claim 10, wherein the at least one of the patient leads is a lead that stimulates a left ventricle of the patient's heart.

12. The method of claim 10, wherein the blood biochemical is B-type Neurouretic Peptide (BNP).

13. A method for optimizing cardiac resynchronization therapy (CRT), comprising:
conducting a baseline measurement of a physical parameter comprising concentration of a blood chemical of a patient before initiating CRT;
performing an implantation process including locating the pacing leads in the patient, including locating a said pacing lead using a lead delivery catheter having means for measuring said physical parameter;
initiating CRT on the patient using the pacing leads;
using the lead delivery catheter to measure the physical parameter of the patient after initiation of the CRT;
comparing the measured physical parameter after initiation of the CRT to the baseline measure of the physical parameter to analyze the patient's response to the CRT; and
based upon the comparison of the measured physical parameter to the baseline measure of the physical parameter, adjusting the CRT during the implantation process to improve the patient's analyzed response to the CRT.

14. The method of claim 13, wherein the chemical in the patient's blood comprises B-type Neurouretic Peptide (BNP).

15. The method of claim 13 wherein adjusting the CRT comprises repositioning a said pacing lead.

16. The method of claim 13, wherein the at least one of the pacing leads is located to stimulate the patient's left ventricle.

17. The method of claim 13, wherein adjusting the CRT comprises adjusting at least one of an AV time interval and a VV time interval.

* * * * *